United States Patent [19]

Koenig

[11] 4,084,588
[45] Apr. 18, 1978

[54] PARENTERAL DRUG STORAGE DEVICE WITH CLOSURE PIERCING COUPLING MEMBER

[75] Inventor: Elmer A. Koenig, Kirkwood, Mo.

[73] Assignee: Sherwood Medical Industries Inc., St. Louis, Mo.

[21] Appl. No.: 668,388

[22] Filed: Mar. 19, 1976

[51] Int. Cl.² ............................................. A61M 5/00
[52] U.S. Cl. ............................ 128/218 R; 128/272.3
[58] Field of Search ....... 128/218 R, 218 D, 218 DA, 128/218 M, 215, 220, 221, 272, 272.3; 215/250, 257; 206/222

[56] References Cited

U.S. PATENT DOCUMENTS

| 2,661,740 | 12/1953 | Hickey | 128/218 R |
|---|---|---|---|
| 3,336,924 | 8/1967 | Sarnoff et al. | 128/272.3 |
| 3,375,825 | 4/1968 | Keller | 128/221 |
| 3,405,712 | 10/1968 | Pierick | 128/218 M |
| 3,406,686 | 10/1968 | Keller | 128/218 R |
| 3,739,779 | 6/1973 | Pfleger | 128/218 DA |
| 3,884,229 | 5/1975 | Raines et al. | 128/218 DA |

FOREIGN PATENT DOCUMENTS 2,442,856  11/1975  Germany ................ 128/272.3

Primary Examiner—John D. Yasko
Attorney, Agent, or Firm—Stanley N. Garber; William R. O'Meara

[57] ABSTRACT

A syringe or other container which may be prefilled with a parenteral drug has an end closed by a pierceable seal that is engaged between the end of the syringe barrel and a plastic sealing cap. A coupling member is disposed for sliding movement on the cap. The coupling member has a pointed end for piercing the seal, and a luer coupling portion at the opposite end for connection with a coupling element associated with another device, such as a catheter or needle cannula.

27 Claims, 4 Drawing Figures

PARENTERAL DRUG STORAGE DEVICE WITH CLOSURE PIERCING COUPLING MEMBER

BACKGROUND OF THE INVENTION

This invention relates to containers for parenteral drugs and, more particularly, to parenteral drug storage devices of the type that can be prefilled with a drug for storage and which has means for arming the device prior to administration of the drug.

Parenteral drugs are often packaged and stored in glass ampoules or vials. Ampoules are used by breaking the necked portion and inserting the needle of a syringe into the main body portion to draw the desired quantity of drug into the syringe. Vials are used by inserting the needle of a syringe through the rubber stopper on the vial. There are certain undesirable aspects associated with these devices. For example, both a syringe and an ampoule or vial are required. There is the danger of injecting glass or stopper particles into the patient since the same needle is used to draw the drug into the syringe and to inject the drug. The additional handling of the parts in order to fill the syringe increases the danger of contamination. Also, the time required to fill the syringe, particularly where the dosage is of relatively large volume, can be highly undesirable, especially in emergency cases.

Prefilled syringes generally have a double-ended needle cannula which is shifted relative to the barrel containing the drug to arm the syringe for use. While the drug may be conveniently stored in the syringe barrel, these devices usually employ a glass barrel having a generally relatively expensive necked-down portion with a flange, and a cap clamping a pierceable seal to the barrel end and being fitted over the flange, for example, as disclosed in U.S. Pat. No. 3,406,686 and 3,375,825.

Both of the above-mentioned systems are also generally limited in use to applications where direct infusion of the drug is accomplished through the needle connected to the barrel. Neither system is generally suitable for use with other drug administration devices such as catheters, intravenous administration or infusion devices employing catheters, or other conventional fluid couplers.

SUMMARY OF THE INVENTION

It is therefore an object of the present invention to provide a new and improved parenteral drug storage device, such as a syringe, which is economical, simple to use, and which can be readily armed for administering the drug to a patient, and which is adapted to selectively receive various types of administration devices.

Another object is to provide a parenteral drug storage device which can be prefilled with a parenteral drug for long term storage, preserves the potency and sterility of the drug during storage, and which has a safe means for transferring the drug to the patient with a minimum chance of contaminating the drug.

In accordance with one form of the present invention, a container for a drug is provided with an opeing at one end, a seal closing the opening, a cap member secured to the container, and a coupling member disposed for sliding movement relative to the cap member which has a seal piercing portion at one end and a coupling portion at the other end for receiving a fluid coupling element for administering the drug.

These, as well as other objects and advantages of the present invention, will become apparent from the following detailed description and drawing.

DESCRIPTION OF THE PREFERRED EMBODIMENT

Figure 1:
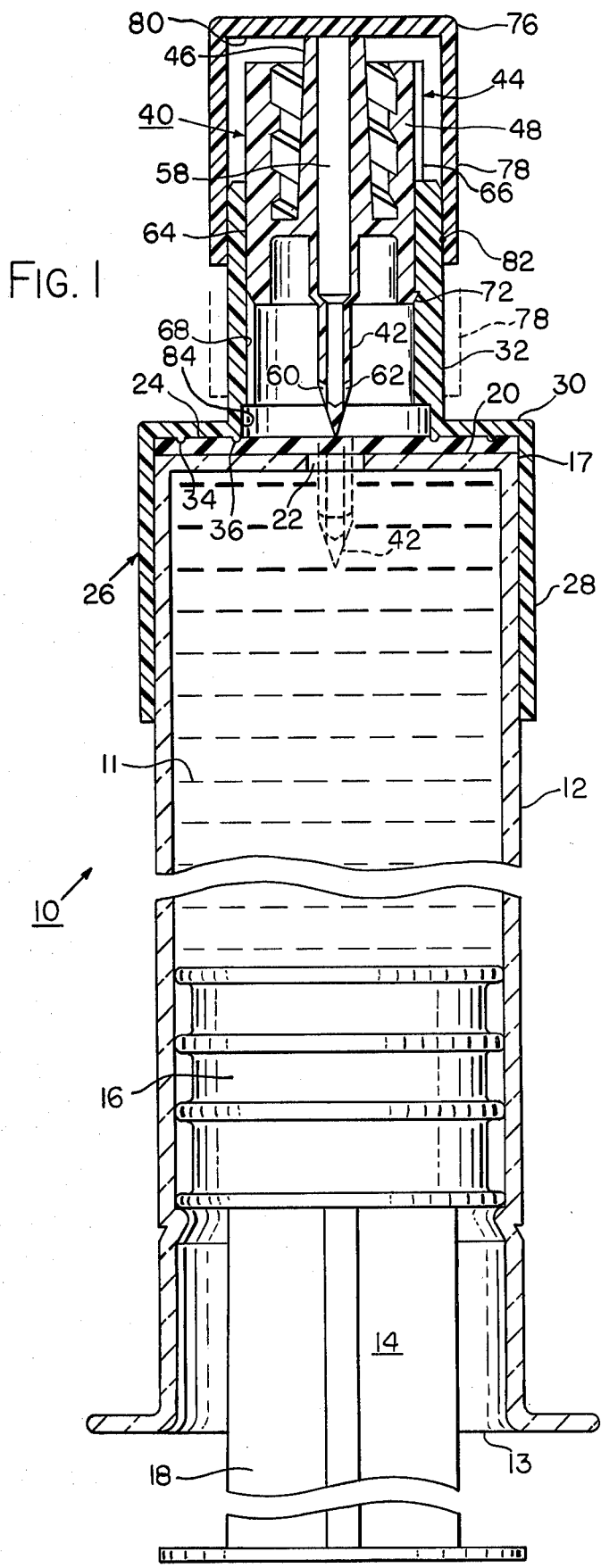
FIG. 1 is an elevational cross-sectional view of a syringe in accordance with a preferred embodiment of the present invention.

Referring now to the drawing, and particularly to FIG. 1, there is shown a syringe 10 capable of storing a parenteral drug 11, such as a drug in liquid form. The syringe includes a cylindrical syringe barrel 12, preferably of glass, having an open proximal or lower end 13 receiving a plunger 14 having a sealing piston 16, such as of rubber, and a piston rod 18 connected, such as by threads (not shown), to the piston 16. The upper or distal end 17 of the barrel 12 has a radially inwardly extending, substantially flat, end portion 20 with a central opening 22 therein. The opening 22 is closed by a seal member 24. The seal member 24 is formed of a suitable elastomer such as silicone or natural rubber. The seal member may be formed, for example, of a silicone rubber with a coating of polytetrafluoroethylene, such as Teflon or the like, on the interior side of it so that the drug which may be stored within the barrel 12 is not affected or contaminated by the rubber seal member.

The seal member 24 is clamped against the exterior side of the barrel end portion 20 by a cap 26 with the seal member covering and closing the opening 22. The cap 26 has a lower cylindrical portion 28 integral with a radially inwardly extending shoulder portion 30 which is integrally connected with a distally extending cylindrical sleeve 32 at the upper portion of the cap. A pair of circular ribs or rings 34 and 36 extend downwardly from the inner surface of portion 30 which engage and extend into the seal member 24. The cap 26 may be made by the injection molding of a suitable plastic, for example, polypropylene. It is formed such that the lower cylindrical portion 28 has an inside diameter slightly less than the outside diameter of the glass barrel 12. When applying the cap 26, it is preferable to heat the cap to slightly soften it and then apply it by moving it down onto the upper end of the barrel 12 with the seal 24 between the barrel end portion 20 and radial shoulder portion 30 of the cap. As the cap 26 cools, it shrinks so that upon cooling, the cap provides a good tight fit with the barrel and the seal 24 is sealingly clamped between the cap and barrel to provide a liquid-tight seal for the distal end of the barrel. The rings 34 and 36 provide higher pressure areas for better sealing and reduce the tendency of the seal to slide toward its center during needle penetration.

Figure 2:
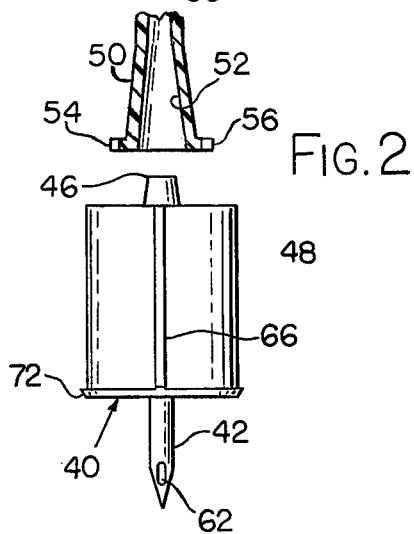
FIG. 2 is an elevational view, on a reduced scale, of the coupling member of the syringe of FIG. 1, and a fragmentary sectional view of a coupling element connectable with the coupling member.

The cap 26 supports a movable syringe arming and fluid coupling member 40, the member 40 being connected to the cap for sliding movement relative to the cap. Member 40 is preferably a single-piece member having a needle or pointed portion 42 at the proximal or lower end, and a fluid coupling portion 44 at the distal or upper end. The coupling portion 44 is shown as a luer lock coupler of conventional configuration which has a luer tapered central portion 46 and a concentric, radially outer, internally threaded luer locking portion 48. Coupler 44 is generally referred to as a male luer lock connector and is adapted to receive a complementary coupling element such as a female luer lock connector, partially shown in FIG. 2 at 50, and which is associated with other apparatus for conveying fluid from the barrel to the patient. The luer lock coupling element 50, which is of conventional construction, has a luer tapered bore portion 52, and a pair of diametrically opposed radial lugs 54 and 56 which serve as threads. The lugs cooperate with the internal threads on locking portion 48 of the coupling member 40 to cause the bore 52 to be drawn into fluid tight engagement with the lure tapered portion 46 when rotated. For example, a hypodermic needle having a female lure lock connector like connector 50 may be connected to coupling portion 44, or medical tubing or a catheter, such as an intravenous catheter that is provided with a luer lock coupling element like element 50 may be connected to the coupling portion 44. If desired, a simple luer slip connector without lugs may be employed to provide a fluid tight slip fit with the center portion 46. Also, coupling portion 44 may be a simple slip fit type connector without internal threads. The coupling member 40 has a central lumen 58 extending through the luer tapered portion 46 and needle 42. The needle is provided with a pair of opposed side openings or holes 60 and 62 which connect with lumen 58. Coupling member 40 is a single-piece molded member of a suitable plastic, such as a relatively hard polycarbonate.

In the illustrated embodiment, the arming and coupling member 40 is sized to slide on the cylindrical portion 32 of cap 26. The member 40 is slidable within the cap from an initial or normal unarmed position, the position shown in the drawing, to an armed position wherein an end portion of the needle 42 and the holes 60 and 62 are disposed within the barrel 12 so that the drug 11 within the barrel 12 is in fluid communication with lumen 58, the lower end of the needle shown in phantom in its armed position.

Figure 3:
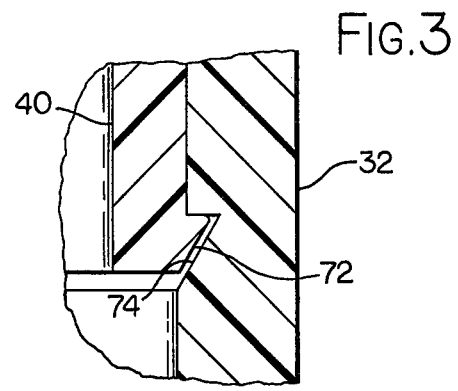
FIG. 3 is a fragmentary cross-sectional view, on an enlarged scale, of portions of the cap and coupling members 26 and 40 of FIG. 1.
Figure 4:
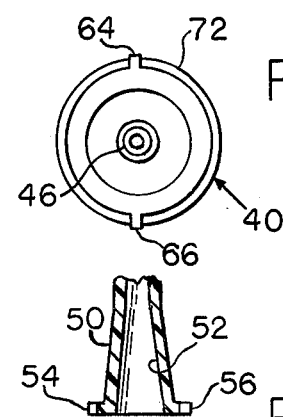
FIG. 4 is a top end view of the coupling member of FIG. 2.

Referring also to FIGS. 3 and 4, the coupling member 40 has a generally cylindrical outer surface with a pair of diametrically opposed axially extending keys or ribs 64 and 66 which are slidable in a pair of diametrically opposed, axially extending, grooves or keyways 68 (one shown) in the cylindrical portion 32 of cap 26. This key and keyway arrangement prevents the member 40 from rotating on its axis when a female luer coupling element, such as element 50, is rotated into sealing engagement with the member 46. In order to locate and maintain the member 40 in its unarmed position, it is provided with a radially outwardly extending, annular rib or skirt 72 which has an outer diameter slightly greater than the inner diameter of cap portion 32 but which is resilient enough to allow the insertion and movement of member 40 in the cylindrical portion 32. The skirt 72 snaps into an annular groove 74 formed in the side wall of the cylindrical portion 32 intermediate its ends, as best seen in FIG. 3, to hold and maintain the member 40 in the unarmed position.

A protective arming cap or end closure 76, preferably of a suitable plastic such as polypropylene, is shown having a cylindrical portion 78 with an inner diameter such that it slides over the outer surface of the cylindrical portion 32 of cap 26, and an upper integral radial end wall 80. The end closure cap 76 is preferably heat staked or spot-welded to cap 26, such as indicated at 82. When it is desired to arm the syringe, the cap 26 is merely rotated to break the spot-weld 82 and then moved axially toward the barrel 12. The upper end of the central luer tapered portion 46 of the member 40 extends above the upper end of the threaded portion 48 and engages the inner side of the wall 80 of closure cap 76. When the cap 76 is moved axially, it causes the member 40 to move downwardly with the skirt 72 being forced out of groove 74 (FIG. 3) and to slide along the inner wall of the cylindrical portion 32 until it engages the seal member 24. During this downward movement, the needle 42 pierces the seal member to place the lumen 58 in fluid communication with the fluid 11 in the barrel 12. The skirt 72 enters a lower undercut or groove 84 in cap portion 32 to ensure that the coupling member 40 remains in the armed position during use of the syringe.

After the end closure cap 76 has been used to arm the syringe, it is removed and a coupling element, such as element 50, of the device to which the luer lock coupling member 44 is to be connected, is attached. The syringe plunger 14 may then be moved distally relative to the barrel 12 to cause the liquid drug 11 within the cylindrical barrel 12 to flow into the holes 60 and 62 of the needle 42, through lumen 58, to coupling portion 44 and to the apparatus connected to element 50.

The coupling member 40 provides a simple and effective member which is capable of arming the syringe and which permits different types of medicament applying, infusion devices or coupling elements, such as 50, to be quickly and readily coupled in fluid communication with the fluid in the syringe barrel. No transfer of fluid from a container to the syringe at the time of use is required and the medicament can be directly stored in the syringe 10. This avoids the disadvantages previously mentioned in connection with systems requiring the transfer of fluid. The needle 42 can be formed so that it does not tend to core the seal member since it is not subsequently inserted into a patient. Also, the simple and effective construction of cap 26 and seal member 24, and the heat staking of it to the barrel 12, provide a highly effective puncturable seal assembly for the syringe 10. The end wall 20 of the barrel is substantially flat so that it is more economically made than the necked type. The hole 22 can be post-formed in the wall 20.

The parenteral drug storage device of the present invention is especially well suited in the form of a syringe, as is shown and described in the preferred embodiment herein. However, if desired, other devices such as vials can be advantageously provided with closures and arming parts similar to those of syringe 10. For example, a vial container having an integrally closed bottom can be advantageously provided at the open end with closure and arming members like members 24, 26, 40, and 76. In such case, the vial is armed in the same manner as described with syringe 10. The luer slip portion of the coupling member in such case may be of the female type so as to receive a male luer slip member such as commonly provided on the end of a syringe barrel. After such syringe barrel is filled, a hypodermic needle may be attached for injection purposes.

As various changes could be made in the above construction without departing from the scope of the invention, it is intended that all matter contained in the above description or shown in the accompanying drawing shall be interpreted as illustrative and not in a limiting sense.

What is claimed is:

1. A parenteral drug storage device comprising a container for receiving the parenteral drug, movable piston means disposed in said container and closing one end thereof, said container having an opening at the opposite end, cap means connected to said opposite end of said container in fixed relation thereto, separate pierceable seal means sealingly closing said opening, and a movable fluid coupling member connected to said cap means having a fluid coupling portion with a luer slip connector at one end thereof adapted for direct contact fluid tight connection with a complementary luer fluid coupling element for passing drug from said container to the complementary coupling element, a seal piercing portion at the opposite end thereof for piercing said seal means, and means connecting said couplng portion in fluid communication with said piercing portion, said fluid coupling member being slidable relative to said cap means from an initial unarmed position to an armed position wherein said piercing portion has pierced said seal means and has moved through said opening to thereby connect said coupling portion in fluid communication with the interior of said container, said piston means being movable toward said opposite end of said container for forcing parenteral drug from said container into said coupling portion.

2. The device of claim 1 wherein said coupling member is a single-piece member of plastic.

3. The device of claim 1 wherein said fluid coupling portion includes a threaded portion surrounding said slip connector to form a luer lock connector.

4. The device of claim 1 wherein said seal means is disposed between a portion of said cap means and the exterior of said opposite end of said container.

5. The device of claim 4 wherein said cap means is a heat staked shrunken cap with said seal clamped between said cap and said container.

6. The device of claim 1 wherein said cap means includes a generally cylindrical portion frictionally engaging the outer periphery of said container adjacent said opposite end thereof.

7. The device of claim 6 wherein said cap means includes a second cylindrical portion distally of the distal end of said container, and said fluid coupling member is axially slidable on said second portion between said unarmed and armed position.

8. The device of claim 7 wherein said second cylindrical portion and said fluid coupling member have complementary groove and bead means in fitting relation when said fluid couplng member is in the unarmed position.

9. The device of claim 6 wherein said fluid coupling member and said other cylindrical portion have complementary key and keyway means preventing relative rotation between said fluid coupling member and said cap means.

10. The device of claim 9 wherein said fluid coupling member comprises a unitary member of synthetic plastic.

11. The device of claim 1 further including a closure member extending over and engageable with the distal end of said fluid coupling member to close said coupling portion, said closure member being proximally slidable to move said fluid coupling member from the unarmed to the armed position.

12. The device of claim 1 wherein said fluid coupling member comprises a generally cylindrical member, and said means connecting said coupling portion in fluid communication with said piercing portion which includes an axial lumen in said fluid coupling member, said piercing portion having a pointed end with openings connecting the exterior of said piercing portion with said lumen.

13. The device of claim 12 wherein said fluid coupling member is a single-piece member of plastic.

14. The device of claim 13 wherein said cap means is of plastic, and said seal means is of an elastomeric material.

15. A syringe comprising a barrel containing a parenteral drug having an open proximal end, and a distal end having an opening therein, slidable piston means in said barrel closing said proximal end and capable of forcing said parenteral drug from said barrel when the syringe is in use, cap means fixedly connected to the distal end of said barrel, separate pierceable seal means clamped between said cap means and said distal end sealingly closing said opening, and a movable fluid coupling member having a fluid coupling portion with a luer slip connector at the distal end thereof adapted for direct contact fluid tight connection with a complementary luer slip fluid coupling element for passing drug from said barrel to the complementary coupling element, a seal piercing portion at the proximal end thereof for piercing said seal means, and lumen means connecting said coupling portion in fluid communication with said piercing portion, said fluid coupling member being connected to said cap means and slidable relative thereto from an initial unarmed position to an armed position wherein said piercing portion has pierced said seal means and has entered said opening to thereby connect said coupling portion in fluid communication with the interior of said barrel.

16. The syringe of claim 15 wherein said coupling member is a single-piece member of plastic and.

17. The syringe of claim 15 wherein said seal means is disposed between a portion of said cap means and the exterior of the distal end of said barrel.

18. The syringe of claim 17 wherein said cap means has a first generally cylindrical portion surrounding and engaging the outer periphery of said barrel at the distal end thereof, a radial shoulder portion integral with said first cylindrical portion and engaging the distal side of said seal means, and a second generally cylindrical portion integral with and extending distally from said shoulder portion, said coupling member being slidably connected to said second cylindrical portion.

19. The syringe of claim 18 wherein said cap means is plastic and said barrel is of glass.

20. The syringe of claim 18 further including an end closure frictionally engaged with said second cylindrical portion of said cap means for covering the distal end of said coupling portion.

21. The syringe of claim 20 wherein said parenteral drug is a liquid drug in said barrel and said piston is an elastomeric piston in said barrel on the proximal side of said drug, and said coupling member is slidable along a straight longitudinal line.

22. The syringe of claim 17 wherein said cap means is a heat staked shrunken cap clamping said seal between said cap means and said barrel.

23. The syringe of claim 16 wherein said fluid coupling portion includes a threaded portion surrounding said slip connector to form a luer lock connector.

24. The syringe of claim 16 wherein said luer lock connector is of the male type.

25. The syringe of claim 15 further including a coating on the proximal side of said seal means to prevent contamination of said parenteral drug by said seal means, and said seal means being clamped between portions of said cap means and said barrel.

26. The syringe of claim 1 wherein said cap means is a radially shrunken cap having a cylindrical portion tightly engaging an outside peripheral portion of said container adjacent the distal end of said container.

27. The syringe of claim 26 wherein said cap means has an integral shoulder portion extending from said cylindrical portion radially inwardly over a portion of the distal side of said seal means.

* * * * *